(12) United States Patent
Molenaar et al.

(10) Patent No.: US 12,226,710 B2
(45) Date of Patent: Feb. 18, 2025

(54) CHROMATOGRAPHIC SEPARATION OF METALS USING DOTA-BASED CHELATORS

(71) Applicant: NUCLEAR RESEARCH AND CONSULTANCY GROUP, Petten (NL)

(72) Inventors: Thomas Jacobus Maria Molenaar, Petten (NL); Sander De Groot, Petten (NL)

(73) Assignee: STICHTING NUCLEAR RESEARCH AND CONSULTANCY GROUP, Petten (NL)

( * ) Notice: Subject to any disclaimer, the term of this patent is extended or adjusted under 35 U.S.C. 154(b) by 420 days.

(21) Appl. No.: 17/843,542

(22) Filed: Jun. 17, 2022

(65) Prior Publication Data

US 2022/0401856 A1 Dec. 22, 2022

Related U.S. Application Data

(63) Continuation of application No. PCT/EP2020/086847, filed on Dec. 17, 2020.

(30) Foreign Application Priority Data

Dec. 20, 2019 (EP) .................................... 19218962
Apr. 3, 2020 (EP) .................................... 20167932

(51) Int. Cl.
*B01D 15/38* (2006.01)
*C07D 273/00* (2006.01)
(Continued)

(52) U.S. Cl.
CPC ....... *B01D 15/3828* (2013.01); *C07D 273/00* (2013.01); *C07D 471/08* (2013.01);
(Continued)

(58) Field of Classification Search
None
See application file for complete search history.

(56) References Cited

U.S. PATENT DOCUMENTS

| 6,716,535 | B1 | 4/2004 | Plundrich et al. |
| 2014/0294700 | A1 | 10/2014 | Marx et al. |

FOREIGN PATENT DOCUMENTS

| EP | 3 492 460 | 6/2019 |
| WO | WO-2007/104135 | 9/2007 |

OTHER PUBLICATIONS

Ferreira et al., "Evaluation of Bifunctional Chelates for the Development of Gallium-Based Radiopharmaceuticals," Bioconjugate Chem, 2010, 21, 531-536.

(Continued)

*Primary Examiner* — Anthony M Liang
(74) *Attorney, Agent, or Firm* — Foley & Lardner LLP (57) ABSTRACT

The present invention relates to use of a chelating compound for chromatographic separation of rare earth elements, actinides, and/or s-, p- and d-block metals, and to a method of chromatographic separation of chelates of rare earth elements, actinides and/or s-, p- and d-block metals from a mixture of at least two metal ions. The method is characterized in that it comprises the following steps:
  (a) providing a mixture of at least two different metal ions chosen from rare earth metal ions, actinide ions and/or s-, p- and d-block metal ions,
  (b) contacting metal ions comprised in said mixture to with at least one compound of general formula (I) as defined in any one of the preceding claims to form chelates;
  (c) subjecting the chelates from step (b) to chromatographic separation, wherein optionally at least one separated metal chelate obtained in step (c) can be subjected to at least one further chromatographic sepa-
(Continued)

ration in order to increase the purity of the at least one separated metal chelate; and, optionally, (d) obtaining the metal from the at least one separated metal chelate.

16 Claims, 7 Drawing Sheets

(51) Int. Cl.
- *C07D 471/08* (2006.01)
- *C22B 3/22* (2006.01)
- *C22B 59/00* (2006.01)
- *C22B 60/02* (2006.01)

(52) U.S. Cl.
CPC ............... *C22B 3/22* (2013.01); *C22B 59/00* (2013.01); *C22B 60/02* (2013.01)

(56) References Cited

OTHER PUBLICATIONS

Haraga et al., "Safe and rapid development of capillary electrophoresis for ultratrace uranyl ions in radioactive samples by way of fluorescent probe selection for actinide ions from a chemical library," Analytica Chimica Acta, vol. 1032, Jun. 1, 2018.

International Search Report and Written Opinion for PCT/EP2020/086847 mailed Mar. 11, 2021.

Suzuki et al., "Facile synthesis and evaluation of C-functionalized benzy-1-oxa-4,7,10-triazacyclododecane-N,N,N-triacetic acid as chelating agent for 111in-labeled polypeptides," Bioorganic & Medicinal Chemistry, 20, 2012, 978-984.

European Search Report on EP 19218962.9 dated Apr. 20, 2022.

Usha Pandey et al., "Investigation on the influence of metal ion impurities on the complexation behavior of generator produced 90Y with different bifunctional chelators", Radiochimica Acta, May 2014, pp. 947-954.

CHROMATOGRAPHIC SEPARATION OF METALS USING DOTA-BASED CHELATORS

CROSS-REFERENCE TO RELATED APPLICATIONS

The present application is a continuation application of PCT/EP2020/086847 filed Dec. 17, 2020, which claims priority to EP 19218962.9 filed Dec. 20, 2019 and claims priority to EP 20167932.1 filed Apr. 3, 2022, the entire contents of all of which are incorporated herein by reference.

TECHNICAL FIELD

The present invention relates to use of a chelating compound for chromatographic separation of rare earth elements, actinides, and/or s-, p- and d-block metals, and to a method of chromatographic separation of chelates of rare earth elements, actinides and/or s-, p- and d-block metals.

BACKGROUND ART

Radionuclides have been successfully adopted for diagnostic applications for decades. In the past ten years, new compounds have been developed that can target diseases such as cancer very specifically. By combining these compounds with radionuclides, diseases such as cancer can be imaged, allowing accurate diagnosis, as a basis for optimal treatment. The targeting accuracy of these compounds has now come to a level, that radionuclides can be adopted that have a therapeutic effect by locally damaging tissue and cells, largely leaving healthy tissue and cells unharmed. As development of more and more specifically targeting compounds progresses, the combination of imaging and therapy with radionuclides (theranostics) is bound to expand, benefitting the patient with more personalized treatment possibilities that combine efficacy with less side effects.

For therapeutic applications, radionuclides with appropriate properties and specifications are required, specifically with high nuclidic purity, high chemical purity and high specific activity. A possible production route of a radionuclide is by neutron activation of a non-radioactive element generating a radionuclide of the same element. As both target and product radionuclide have the same chemical properties, they cannot be chemically separated and thus the mixture is called 'carrier added' (CA).

Even better characteristics can be achieved by the neutron activation of an element, often enriched in one isotope, leading to transmutation of a part of the atoms to another isotope of another chemical element, which is subsequently (chemically) extracted after irradiation. This so-called 'non-carrier added' (NCA) or 'carrier-free' production route generates the highest purity and highest specific activity product as compared to the CA-route. However, chemical separation of the radioactive product from the irradiated target bulk is extremely complicated:

The elements to be separated can be chemically very similar, for example neighboring elements from the lanthanide family, making effective separation difficult.

By activation, only a very tiny amount of the desired isotope is generated in the source material. It is challenging to extract these micro amounts of the desired isotope from the macro amounts of source material with adequate efficiency.

The material decays quickly, hence separation needs to take place as fast as possible to be able to maintain the high specific activity required.

The materials are radioactive, impacting the infrastructure required to work with the material safely, and which can influence the stability and efficiency of separation processes.

To be able to meet the increasing demand of high quality radionuclides for therapy, robust, quick, safe and efficient separation of (radioactive) elements is required.

Focusing on the complex separation of rare earth elements, and specifically lanthanides, multiple methods and techniques have been developed. The currently most adopted method is by the use of (cat)ion exchange chromatography columns, such as disclosed in EP2546839 (US2014294700, ITG) or U.S. Pat. No. 6,716,535 (Batelle). In the latter case first ytterbium is eluted from an LN-resin containing chromatographic column using moderately concentrated hydrochloric acid, and subsequently 177Lu is obtained by using higher concentrated hydrochloric acid. In this case microscopic amounts of 177Lu are separated from macroscopic amounts of ytterbium, a disadvantage of this prior art method is that first the macroscopic component is eluted of which an extreme surplus is present, complicating isolation of later eluted microscopic amounts of 177Lu due to tailing of the macroscopic component. This necessitates repeated separation processes.

Other possibilities are solvent-solvent extraction, making use of the slight differences between extractability from a solvent, liquid membrane extraction (under development), electrochemical separation by selective reduction and (Hg) cathode deposition. These methods are all more or less developed. Nevertheless, despite the multitude of potential separation methods, each of these methods still require a significant development and upscaling effort, and feasibility of these methods to provide a quick, efficient and robust production process remains to be seen. With separation of actinides, and/or s-, p- and d-block metals similar problems are encountered.

Recently a chelator-based method of separation was disclosed in EP3492460 (Polasek), in which complexed metal elements could be separated by chromatographic separation. For this method, DOTA-based chelators were adopted. Although the method has advantages over the abovementioned methods, the used chelators are not yet optimal with respect to separation potential. WO20071014035 discloses a type of polyazamacrocyclic chelators that share an asymmetric structure but is silent on their use as metal chelators for use in chromatographic separation.

It is well known that DOTA-based chelators form highly stable complexes with metals, in particular with lanthanides such as Lu, Yb, Gd and Tb. The success of DOTA and its derivatives is largely due to their ability to form complexes with these metal ions with high thermodynamic stability and extraordinary kinetic inertness. Although the formation of highly stable complexes is of critical importance for bifunctional chelators that are used in clinical or in vivo settings, this stability is a drawback when the chelator is used in a chromatographic separation process after which the chelator needs to be removed.

Moreover, DOTA-derivatives reportedly suffer from slow complex formation at mild conditions requiring the performance of the radiolabeling reaction at elevated temperatures.

Ideally, chelators that are used in a chromatographic separation process of metal elements show fast complexation rates at mild conditions (i.e. room temperature, mild pH, low molar excess), have fast de-complexation rates upon mild acidification, yet are stable under separation conditions. Such qualities, in addition to the separation quality (i.e. the chromatographic resolution of the metal elements to be separated) and initial scalability would increase the speed and ease of the method, thereby increasing the potential for industrial application and scale up.

It is an objective of the present invention to overcome one or more of the abovementioned problems, or at least to provide a useful alternative. It is a further objective of the present invention to provide a separation method which is suitable for quick complexation and subsequent separation of radioactive isotopes from an irradiated source material with great chemical similarity, such as separation of 177Lu from 176Yb, or of 161Tb from 160Gd, and subsequent quick decomplexation of the isotopes from the chelator.

SUMMARY OF THE INVENTION

It has now surprisingly been found that another chelator family is very advantageous in the separation of chemical elements, in particular for the separation of very similar elements. These chelators form stable complexes with metal elements very quickly as compared to DOTA, whilst their stability in vivo is less than that of DOTA-derivatives. For (upscaled) separation processes the quick complexation and convenient decomplexation of this chelator family is an advantage compared to DOTA, whilst stability in vivo is not relevant for this application.

The chelator family shows different retention times on a chromatographic column, also for elements which are chemically very similar, such as Ytterbium and Lutetium, and Terbium and Gadolinium. The chelator family also shows advantageous reversal of the order of elution: first the trace (desired) element elutes, followed by the bulk element. This is an unexpected find in view of the similarity between the present chelators and the known chelators (DOTA, EP3492460). Furthermore, it was found that the present family of chelators is capable of forming isomeric complexes. While this seems disadvantageous at first as the presence of two isomers is very likely to complicate the separation process, it was unexpectedly found to be an advantage in the separation process as the loading of the chromatographic column can be increased to higher levels compared to chelators in the art that do not form isomeric complexes.

The present family of chelators can therefore advantageously be used for chromatographic separation of radiometals.

In particular, the present invention discloses the use of a compound of compound of general formula (I)

wherein

A is N or C substituted with one of H, halogen (Cl, Br, F), $SO_3H$, $C_{1-4}$ alkyl, aryl, hetaryl, C—O—$C_{1-16}$ alkylamino, Z and $Z^1$ independently are N or C substituted with one of H, halogen (Cl, Br, F), $SO_3H$, $C_{1-4}$ alkyl, aryl, hetaryl, C—O—$C_{1-16}$ alkylamino, E=O, S or P;

$R_1$ is independently substituted or unsubstituted $C_{4-15}$alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)$(CH_2)_{0-3}$ $CH_3$, $C_{2-5}$carboxyl, —$(CH_2)_{1-3}$C(O)$(CH_2)_{0-3}CH_3$, nitro, amino, thiol, succinimide, maleimide, aminooxyl, acetylene, $N_3$, acetamino, azide, —C(O)O$(CH_2)_{1-3}CH_3$, —OC(O)$(CH_2)_{0-3}CH_3$, halogen, $C_{1-5}$alkynyl, and NCS; and a=0-5, for chromatographic separation of rare earth elements, actinides, and/or s-, p- and d-block metals.

The present invention further discloses a method of chromatographic separation of rare earth elements, actinides and/or s-, p- and d-block metals, from a mixture of at least two metal ions, characterized in that it comprises the following steps:
(a) providing a mixture of at least two different metal ions chosen from rare earth metal ions, actinide ions and/or s-, p- and d-block metal ions,
(b) contacting metal ions comprised in said mixture with at least one compound of general formula (I) as defined in any one of the preceding claims to form chelates;
(c) subjecting the chelates from step (b) to chromatographic separation, wherein optionally at least one separated metal chelate obtained in step (c) can be subjected to at least one further chromatographic separation in order to increase the purity of the at least one separated metal chelate;

and, optionally, (d) obtaining the metal from the at least one separated metal chelate.

The advantage of chromatographic separation using the particular chelator family embodied by general formula (I) is that the complexation and separation process is very quick, and (de-)complexation is very easy. Furthermore, the desired (minor) element is eluted first compared to the major element.

These aspects greatly facilitate up scaled separation processes to produce carrier-free radionuclides.

The chelator with general formula (I) may be used to separate a mixture of at least two elements, which elements are rare earth elements, actinides and/or s-, p- and d-block metals. For example, the chelator can be used for the separation of an isotope of an element with atomic number n+1 from an irradiated sample of an isotope of an element with atomic number n (also called neighboring elements, i.e. neighboring in the periodic table), such as separation of Lu-177 from irradiated Yb-176. In the latter example, after irradiation of Yb-176 with neutrons in a nuclear reactor, a mixture of small amounts of radioactive Lu-177 is formed in a Yb-bulk at an initial ratio of approximately 5000:1. This large ratio, in addition to the extremely similar chemical and physical properties of the neighboring elements, in this case the lanthanides Yb and Lu, makes the separation of the radioactive element from the bulk very difficult.

The method presented in this invention is comparable to that described in EP3492460. However, the chelator of the present invention results in a different metal-chelate complex with superior chelating properties with respect to e.g.

speed and temperature, as well as enhanced separation potential, favorable elution order (desired product first), and enlarged differences in retention times. Decomplexation by acidification is fast, with only small amounts of acid necessary to decomplex and remove the chelator.

DESCRIPTION OF EMBODIMENTS

In the present invention, a compound of general formula (I)

A is N or C substituted with one of H, halogen (Cl, Br, F), $SO_3H$, $C_{1-4}$ alkyl, aryl, hetaryl, C—O—$C_{1-16}$ alkylamino, Z and $Z^1$ independently are N or C substituted with one of H, halogen (Cl, Br, F), $SO_3H$, $C_{1-4}$ alkyl, aryl, hetaryl, C—O—$C_{1-16}$ alkylamino, E=O, S or P;

$R_1$ is independently substituted or unsubstituted $C_{4-15}$alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)(CH$_2$)0-3CH3, $C_{2-5}$carboxyl, —(CH$_2$)$_{1-3}$ C(O)(CH$_2$)$_{0-3}$CH$_3$, nitro, amino, thiol, succinimide, maleimide, aminooxyl, acetylene, $N_3$, acetamino, azide, —C(O)O(CH$_2$)$_{1-3}$CH$_3$, —OC(O)(CH$_2$)$_{0-3}$CH$_3$, halogen, $C_{1-5}$alkynyl, and NCS; and a=0-5, is used for chromatographic separation of rare earth elements, actinides, and/or s-, p- and d-block metals.

The principle of chromatographic separation with the chelating compounds of the present invention provides simplified manipulation with rare earth element, actinide and s-, p- and d-block metal radionuclides in solution, their processing and purification. The speed and simplicity of the method is crucial for manipulation with radionuclides, which undergo radioactive decay. When bound to rare earth metal ions, actinide ions and/or s-, p-, or d-block metal ions, the chelators of the present invention respond to even very small differences in the ionic radii of the metals by pronounced differences in polarity of the respective resulting chelates. Because of the varying polarity, the chelates can be separated by conventional chromatography on normal or reversed phase. The metals are thus separated in the form of chelates. Importantly, the chelators disclosed in this invention form chelates that are kinetically inert on the time-scale of the separation process. The kinetic inertness effectively protects the radionuclide from additional contamination with other metals, as the radionuclide cannot escape from the chelate nor can it be replaced by another metal ion during the chromatography. Importantly, this property allows using conventional chromatographic columns and instrumentation that consists of metal parts. The separation method of the present invention can be used to separate elements regardless of the particular isotopes of the involved elements.

Rare earth elements as well as actinides and s-, p- and d-block metals offer a broad choice of radionuclides for medical applications and are therefore the object of this invention.

Rare earth elements are the group of elements consisting of scandium—Sc, yttrium—Y, and the lanthanides: lanthanum—La, cerium—Ce, praseodymium—Pr, neodymium—Nd, promethium—Pm, samarium—Sm, europium—Eu, gadolinium—Gd, terbium—Tb, dysprosium—Dy, holmium—Ho, erbium—Er, thulium—Tm, ytterbium—Yb and lutetium—Lu.

Actinides are Actinium—Ac, Thorium—Th, Protactinium—Pa, Uranium—U, Neptunium—Np, Plutonium—Pu, Americium—Am, Curium—Cm, Berkelium—Bk, Californium—Cf, Einsteinium—Es, Fermium—Fm, Mendelevium—Md, Nobelium—No, and Lawrencium—Lr.

S-, p- and d-block metals are preferably II.A, III.A, IV.A, V.A metals and transition metals, more preferably II.A, III.A (Al, Ga, In, Ti), IV.A (Sn, Pb), V.A (Bi), I.B, II.B, and VIII.B group metals, most preferably selected from $Ca^{2+}$, $Fe^{2+}$, $Fe^{3+}$, $Co^{2+}$, $Ni^{2+}$, $Cu^{2+}$, $Zn^{2+}$, $Al^{3+}$, $Pb^{2+}$, $Bi^{3+}$.

The general formula (I) of the present invention is meant to include all isomers, enantiomers and diastereoisomers.

The $R_1$ groups in general formula (I) provide for the required hydrophobicity to gain retention, and therefore also a retention difference between different elements on a column, such as a C18 column. Furthermore, the $R_1$ groups provide for UV visibility, such that the non-radioactive component can easily be located during HPLC purification.

$R_1$ preferably is wherein $R_2$ is independently H, —NCS, —OH, —NH$_2$, —C(O)NH$_2$, —NO$_2$, —(CH$_2$)$_{1-3}$O(CH$_2$)$_{1-3}$CH$_3$, —C(O)O(CH$_2$)$_{1-3}$CH$_3$, —OC(O)(CH$_2$)$_{0-3}$CH$_3$, halogen, —(CH$_2$)$_{1-3}$C(O)(CH$_2$)$_{0-3}$CH$_3$, cyano, $C_{2-5}$carboxyl, thiol, —C(O)(CH$_2$)$_{0-3}$CH$_3$, substituted or unsubstituted $C_{1-15}$alkyl, substituted or unsubstituted $C_{1-15}$alkenyl, substituted or unsubstituted $C_{1-15}$alkynyl, substituted or unsubstituted $C_{4-15}$alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)(CH$_2$)$_{0-3}$ CH$_3$, $C_{2-5}$carboxyl, —(CH$_2$)$_{1-3}$C(O)(CH$_2$)$_{0-3}$CH$_3$, nitro, amino, thiol, succinimide, maleimide, aminooxyl, acetylene, $N_3$, acetamino, azide, —C(O)O(CH$_2$)$_{1-3}$CH$_3$, —OC(O)(CH$_2$)$_{0-3}$CH$_3$, halogen, $C_{1-5}$alkynyl, and NCS; and b=1-4.

or

M is preferably N or
R₁ is preferably located at the following position on the macrocycle:

$R_2$ is preferably chosen from the group consisting of H, —NCS, —OH, —NH₂, —C(O)NH₂, —NO₂, —(CH₂)₁₋₃O(CH₂)₁₋₃CH₃, —C(O)O(CH₂)₁₋₃CH₃, —OC(O)(CH₂)₀₋₃CH₃, halogen, —(CH₂)₁₋₃C(O)(CH₂)₀₋₃CH₃, cyano, C₂₋₅carboxyl, thiol, and —C(O)(CH₂)₀₋₃CH₃.

More preferably, $R_2$ is —NH₂ or —NCS.

Preferably a=1-4, more preferably a=1-3, even more preferably a=1-2, most preferably a=1.

Preferably b=1-3, more preferably b=1-2, most preferably b=1.

In a preferred embodiment, $R_1$ is wherein $R_2$ is
independently H, —NCS, —OH, —NH₂, —C(O)NH₂, —NO₂, —(CH₂)₁₋₃O(CH₂)₁₋₃CH₃, —C(O)O(CH₂)₁₋₃CH₃, —OC(O)(CH₂)₀₋₃CH₃, halogen, —(CH₂)₁₋₃C(O)(CH₂)₀₋₃CH₃, cyano, C₂₋₅carboxyl, thiol, —C(O)(CH₂)₀₋₃CH₃, substituted or unsubstituted C₁₋₁₅alkyl, substituted or unsubstituted C₁₋₁₅alkenyl, substituted or unsubstituted C₁₋₁₅alkynyl, substituted or unsubstituted C₄₋₁₅alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)(CH₂)0-3CH3, C₂₋₅carboxyl, —(CH₂)₁₋₃C(O)(CH₂)₀₋₃CH₃, nitro, amino, thiol, succinimide, maleimide, aminooxyl, acetylene, N₃, acetamino, azide, —C(O)O(CH₂)₁₋₃CH₃, —OC(O)(CH₂)₀₋₃CH₃, halogen, C₁₋₅alkynyl, and NCS;

M is preferably a=1-4;
and b=1-4.

$R_2$ can be located at the ortho (2-), meta (3-) or para or 4-) position vis-à-vis the CH₂ group.

In one embodiment, $R_2$ is preferably located at the para-position with respect to CH₂.

More preferably, the compound of general formula (I) is and even more preferably

In another preferred embodiment, the compound of general formula (I) is and even more preferably

Preferably R₂ is chosen from the group consisting of H, —NCS, —OH, —NH$_2$, —C(O)NH$_2$, —NO$_2$, —(CH$_2$)$_{1-3}$O (CH$_2$)$_{1-3}$CH$_3$, —C(O)O(CH$_2$)$_{1-3}$CH$_3$, —OC(O) (CH$_2$)$_{0-3}$CH$_3$, halogen, —(CH$_2$)$_{1-3}$C(O)(CH$_2$)$_{0-3}$CH$_3$, cyano, C$_{2-5}$carboxyl, thiol, and —C(O)(CH$_2$)$_{0-3}$CH$_3$, and more preferably R$_2$ is —NH$_2$ or —NCS.

Most preferably, the compound of general formula (I) is

Preferably, the rare earth elements, actinides and/or s-, p- and d-block metals are rare earth elements, also called rare earth metals. Rare earth elements are particularly desirable, and particularly useful for medical applications. More preferably, the rare earth elements are lanthanides. Even more preferably, the lanthanides are two neighbouring lanthanides. Even more preferably, the lanthanides are Lu and Yb or Tb and Gd. Most preferably, the lanthanides are Lu and Yb.

In the method of the invention rare earth elements, actinides and/or s-, p- and d-block metals, are separated from a mixture of at least two metal ions, characterized in that the method comprises the following steps:
(a) providing a mixture of at least two different metal ions chosen from rare earth metal ions, actinide ions and/or s-, p- and d-block metal ions,
(b) contacting metal ions comprised in said mixture to with at least one compound of general formula (I) as defined in any one of the preceding claims to form chelates;
(c) subjecting the chelates from step (b) to chromatographic separation, wherein optionally at least one separated metal chelate obtained in step (c) can be subjected to at least one further chromatographic separation in order to increase the purity of the at least one separated metal chelate;
and, optionally, (d) obtaining the metal from the at least one separated metal chelate.

In step a) the mixture of at least two different metal ions may be dissolved in strong acid, evaporated and resuspended in dilute hydrochloric acid, such as from 0.01-0.1 M, preferably 0.02-0.08 M, more preferably from 0.03-0.05 M hydrochloric acid.

Preferably the metal ions are in a form of salts of organic or inorganic acids, oxides, hydroxides and/or carbonates, more preferably selected from the group comprising chloride, bromide, sulfate, nitrate, methanesulfonate, trifluoromethanesulfonate, formate, acetate, lactate, malate, citrate, 2-hydroxyisobutyrate, mandelate, diglycolate, tartarate, oxide, hydroxide and/or carbonate.

Preferably in step b), a solution containing the mixture provided in step a) in the form of metal salts, or a solid phase containing the mixture provided in step a) in the form of metal oxide, hydroxide and/or carbonate, is mixed with a solution of the compound of general formula (I) in molar ratio of metal ions to compound of general formula (I) from 1:0.5 to 1:100; organic or inorganic base is added to the reaction mixture, and the complexation takes place in the solution.

More preferably the chelator of general formula (I) is added to the mixture in a molar ratio of metal ion:chelator between 1:0.5 and 1:100, even more preferably between 1:1 and 1:2, most preferably between 1:1.01-1:1.5 (slight excess).

For example, the pH of the mixture may be increased by adding dilute NaOH or a buffer to a pH between 5-8 at room temperature, resulting in the formation of stable metal-chelator complexes.

Preferably, the chromatography in step c) is column chromatography, thin layer chromatography and/or high-performance liquid chromatography. The resulting mixture of metal-chelator complexes may be loaded onto a chromatographic column, for example RP (reverse phase)-HPLC with a C-8 or C-18 stationary phase and a mobile phase of water and organic modifier and/or TFA if necessary. Due to slight differences in the ionic radius between the metals, the resulting metal-chelator complexes have different lipophilicity and therefore behave differently on a chromatographic column.

The desired metal ion chelate may be collected from the outlet of the chromatographic column with a fraction collector and thus separated from the other metal chelate or metal chelates.

If necessary, the above chromatographic separation process may be repeated with the collected metal ion chelate, e.g. at least twice, to further increase the purity of the product.

After purification, i.e. in step d) the metal ion may be decomplexed from the chelator by acidification. The chelator may then be removed from the metal ion by a further chromatographic separation, leading to a final purified product.

Thus, in the method of chromatographic separation according to the invention, the mixture of at least two different metal ions to be separated comprises at least one rare earth element. More preferably, the mixture comprises two neighbouring lanthanides (i.e. neighbouring in the Periodic Table), more preferably the mixture comprises Lu and Yb, or Tb and Gd, even more preferably 177Lu and 176Yb, or 161Tb and 160Gd.

Most preferably the mixture comprises Lu and Yb, particularly 177Lu and 176Yb. The method of the invention is particularly suitable for the separation of Lu and Yb. Upon chelation, Lu and Yb form two region-isomers in stable ratios of ranging from 10-90 w % to 40-60% (depending on the structure of the chelator) Although this seems a disadvantage at first, the isomerization can be used as an asset to remove a larger portion of the Yb in the first separation round, as the differences in retention times between the isomers are sufficiently large.

For example, step c) may be performed at least twice. When such a multiple column strategy is performed to remove Yb from Lu, the two collected Lu-isomer-fractions may be pooled and reinjected on the next column. This will again result in two Lu-isomers, which can be separated from the Yb-isomers.

Alternatively, the collected first isomer may be de-complexed by acidification, immediately followed by re-complexation by increasing the pH. By doing so, the first Lu-isomer may for 85% be interconverted into the second isomer. The combined Lu-fractions may then almost entirely consist of the second Lu-isomer (98%). This strategy may facilitate fraction collection in subsequent columns.

In a preferred embodiment of the method of the invention, the method comprises a step of enriching the chelate-metal complex with a desired isomer by decomplexing part of the isomeric mixture, for instance by altering the pH (up or down). The less stable chelate isomer will decomplex, thereby providing free metal ions. The free metal ions are recomplexed by reversing the pH in the opposite direction (down or up). The free metal ions will recomplex in the preferred isomeric ratio, thereby increasing the relative amount of the more stable chelate. Thus, in a preferred embodiment, the method further comprises one or more decomplexation-recomplexation cycle(s), preferably by a pH cycle, resulting in isomeric enrichment of the metal-chelate complex.

Typically the Lu complex elutes before the Yb complex. This minimizes Yb-tailing into the Lu-fraction. In other words, the Lu complex can be collected first, with a reduced risk of at the same time collecting any Yb complex which was left behind on the column. In a case where the Yb complex would come off the column first, there would be a chance that, due to the high amount of Yb complex, a part of the Yb complex would still be coming off the column when the desired Lu fraction (which is much less material) would start to come off, thereby polluting the Lu fraction. Thus, the method according to the invention provides for a particularly optimized separation result for this pair of neighboring lanthanides, by effective removal of a large fraction of the undesired isotope or element in each pass, with the desired isotope being collected with high yield. This is especially beneficial in up scaled production scenarios.

BRIEF DESCRIPTION OF THE FIGURES

FIG. 2B: Reinjection of collected Lu-fraction from 2a

EXAMPLES

Example 1. Separation of Lu from Yb-Bulk 39.2 µg of $Lu(NO_3)_3$ enriched in Lu-176 (82%) was irradiated at a neutron flux of $3.7 \times 10^{13}$ n $cm^{-2}$ $s^{-1}$ for 1 hour, resulting in 21 MBq of Lu-177 after 1 day cooling (Activity Reference Time, ART). The $Lu(NO_3)_3$ was dissolved in 0.04 M HCl to a final Lu-metal concentration of 18.4 µg/g and Lu-177 activity concentration of 7.5 MBq/g. This Lu-177 stock was used to create Lu-177-spiked Yb/Lu mixtures.

A representative mixture of Yb/Lu was produced by incubating 146 mg of a 91.33 mg/g Yb-stock solution (13.3 mg Yb=75 µmol) with 140.1 mg of the 18.4 µg/g Lu-stock solution (2.6 µg Lu=0.015 µmol), with a final molar ratio of 5000:1. The mixture thus included 1 MBq of Lu-177 at ART for detection purposes.

The Yb/Lu mixture was then incubated with 450 mg of a 110 mg/g commercially available chelator B501 (p-NH2-

Bn-Oxo-DO3A, Macrocyclics) solution in water (86 μmol), thereby creating a small excess of chelator over total lanthanides of 1:1.1. The pH was raised to 8 by adding 385 μl of NaOH (1 M) and the mixture was incubated for 20 minutes at room temperature, to a final volume of 1.0 gram (1 ml).

Subsequently, different amounts of the reaction mixture were subjected to a Waters RP-HPLC (Acquity) equipped with a Waters C-18 column (4.6×250 mm, 5 μm particles), a UV-detector, gamma detector and automated fraction collector (analytical scale). The chromatography was performed at a 1 ml/min flow rate and isocratic elution with 0.1% TFA in deionized water. Desired fractions were collected for analysis.

Figure 1:
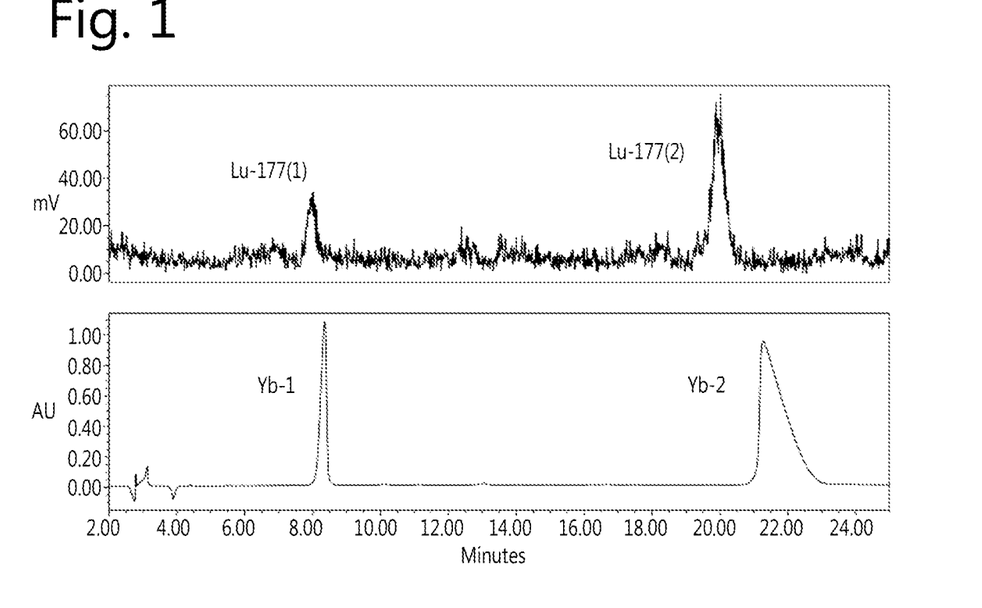
FIG. 1: Typical chromatograph of Yb/Lu-chelates on HPLC C-18 column.

FIG. 1 shows a typical injection of 2.7 μl of the reaction mixture, containing 40 μg total Yb/Lu. Upon chelation, Lu and Yb form two region-isomers in a stable ratio of 15% (first isomer Yb-1)-85% (second isomer Yb-2). The chromatograph shows baseline separation of the Yb (UV) and Lu (radioactivity) of both isomers (Yb-1 and Yb-2).

Example 2. Purification

Figure 2A:
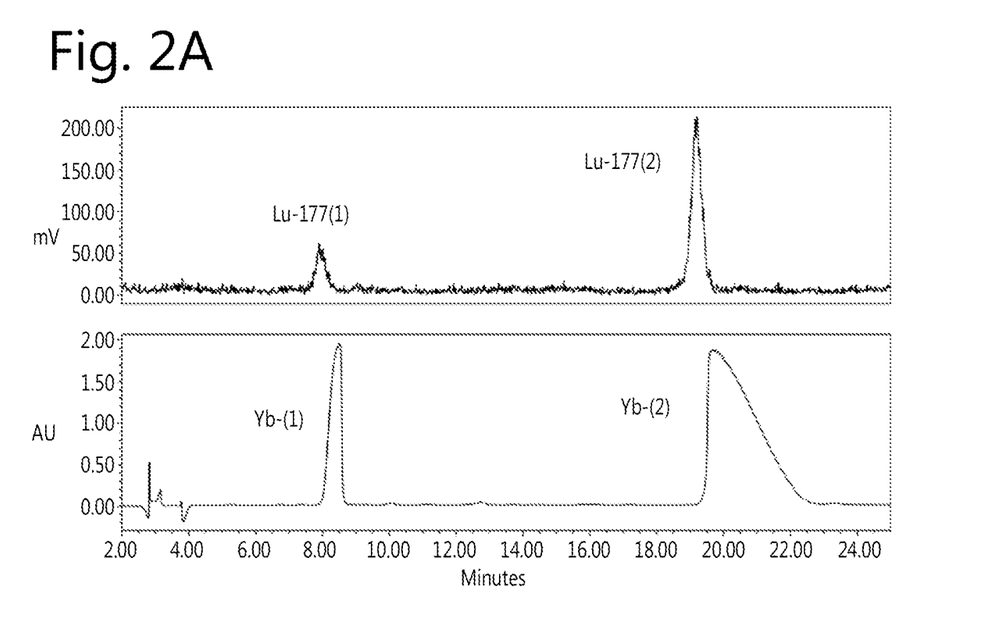
FIG. 2A: First injection of Yb/Lu mix.
Figure 2B:
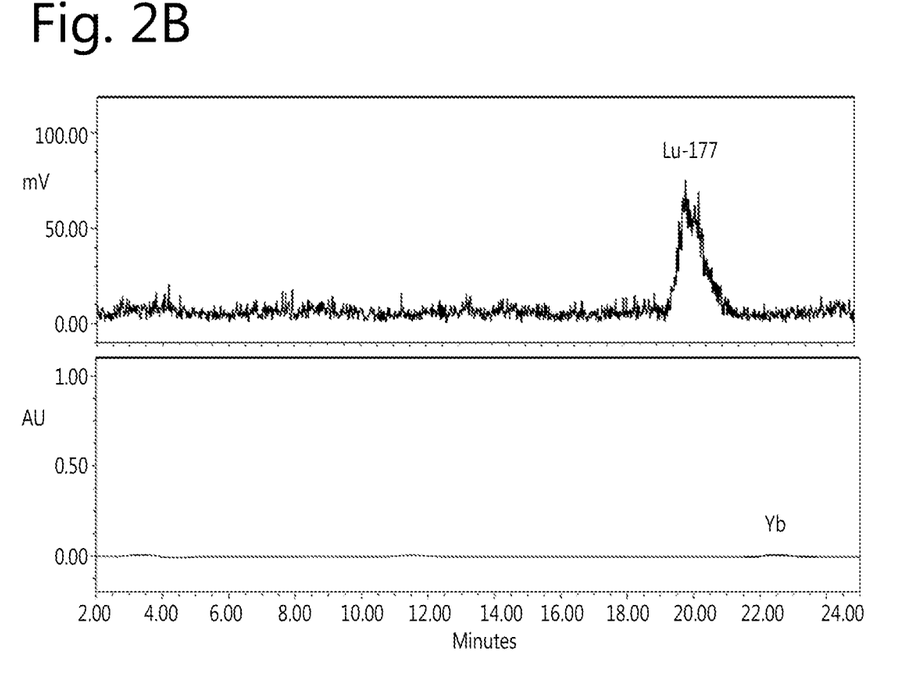

To show the potential of the chelator for separation purposes, a 1-column purification was conducted. FIG. 2A shows the injection of 7.5 μl of the reaction mixture as stated in example 1, this time containing 0.1 mg total Yb/Lu. Both Lu-177 isomers were collected with a total recovery of 90%. Subsequently, the total Lu-177 fraction (1 ml) of the second isomer was reinjected under the same HPLC conditions (FIG. 2B). From the UV-absorbance (210 nm) a 500-fold removal of Yb over the first column was calculated.

Example 3. Retention Times of Lanthanides with Different Chelators

Cold and/or spiked Tb/Gd or Yb/Lu mixes were prepared and subjected to HPLC essentially as described in example 1. The retention times of these lanthanide-chelates ($1^{st}$ and $2^{nd}$ isomer) were then determined by Acquity software. From the differences in retention times, it is clear that both B501(p-NH$_2$—Bn-oxo-DO3A, 1-Oxa-4,7,10-tetraazacyclododecane-5-S-(4-aminobenzyl)-4,7,10-triacetic acid, Macrocyclics) and B505 (p-SCN-Bn-oxo-DO3A, 1-Oxa-4,7,10-tetraazacyclododecane-5-S-(4-isothiocyantobenzyl)-4,7,10-triacetic acid, Macrocyclics), differ only by the functional group placed at the benzyl, provide different retention times for at least the $2^{nd}$ isomer of the metal-chelates.

Example 4

Figure 3:
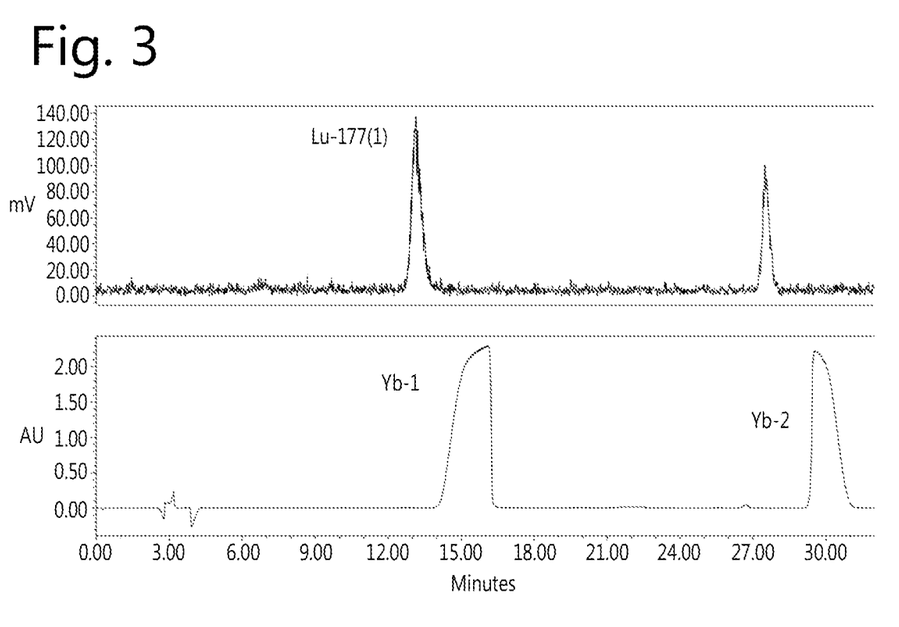
FIG. 3: First injection of Yb/Lu mix for B401
Figure 4:
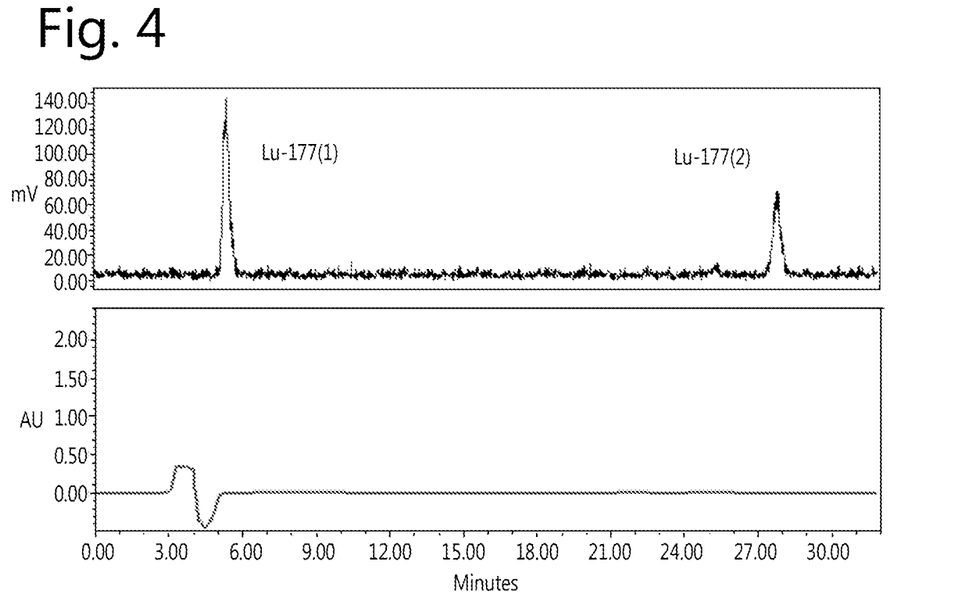
FIG. 4: Reinjection of collected Lu-fraction for B401

A chelate containing a pyridine in the ring structure, B401 (p-NH2-Bn-PCTA, 3,6,9,15-Tetraazabicyclo[9.3.1] pentadeca-1(15), 11,13-triene-4-S-(4-aminobenzyl)-3,6,9-triacetic acid, Macrocyclics) was used in analogous experiments. Upon chelation, Lu and Yb form two region-isomers in a stable ratio of 65% (first isomer Yb-1)-35% (second isomer Yb-2). Retention times were determined with injection of 0.1 mg Yb and injection with 0.1% TFA in water, followed by elution with 0.5% EtOH for 15' followed by 1.5% EtOH. FIG. 3 shows the elution profile and the start of the purification FIG. 4. shows the $2^{nd}$ column in which the $1^{st}$ and $2^{nd}$ isomer are reinjected. Both Lu-177 isomers were collected with a total recovery of 90%. Subsequently, the total Lu-177 (1) fraction (0.9 ml) was reinjected under the same HPLC conditions, followed by the injection of the Lu-177 (2) fraction (0.8 ml). Due to the 7' time difference between the first and second injection, the Lu-177 (1) isomer elutes at 6' (FIG. 3). From the UV-absorbance (210 nm) a >500-fold removal of Yb over the first column was calculated for both isomers. B405, the p-NCS analogue of B401 provides similar results.

TABLE 1

| Lanthanide-chelate | B501 $1^{st}$ isomer | B501 $2^{nd}$ isomer | B505 $1^{nd}$ isomer | B505 $2^{nd}$ isomer | B401 $1^{nd}$ isomer | B401 $2^{nd}$ isomer |
|---|---|---|---|---|---|---|
| Gd | ND | ND | 9.3 | 21.1 | | |
| Tb | ND | ND | 9.3 | 22.2 | | |
| Yb | 8.3 | 20.7 | 8.4 | 22.0 | | |
| Lu | 8.0 | 19.6 | 7.8 | 19.4 | | |
| Yb (1% EtOH)* | 5.5* | 9.1* | 5.5* | 9.5* | | |
| Lu (1% EtOH)* | 5.0* | 8.5* | 5.0* | 8.7* | | |
| Yb (0.5%-1.5%)** | | | | | 16.1** | 29.5** |
| Lu (0.5%-1.5%)** | | | | | 13.1** | 27.5** |

Retention times of
*mobile phase = 0.1% TFA in water with 1% EtOH.
**0.1% TFA with 0.5%-1.5% EtOH-gradient.
All other runs with mobile phase 0.1% TFA in water (without EtOH).

Example 5

Figure 5:
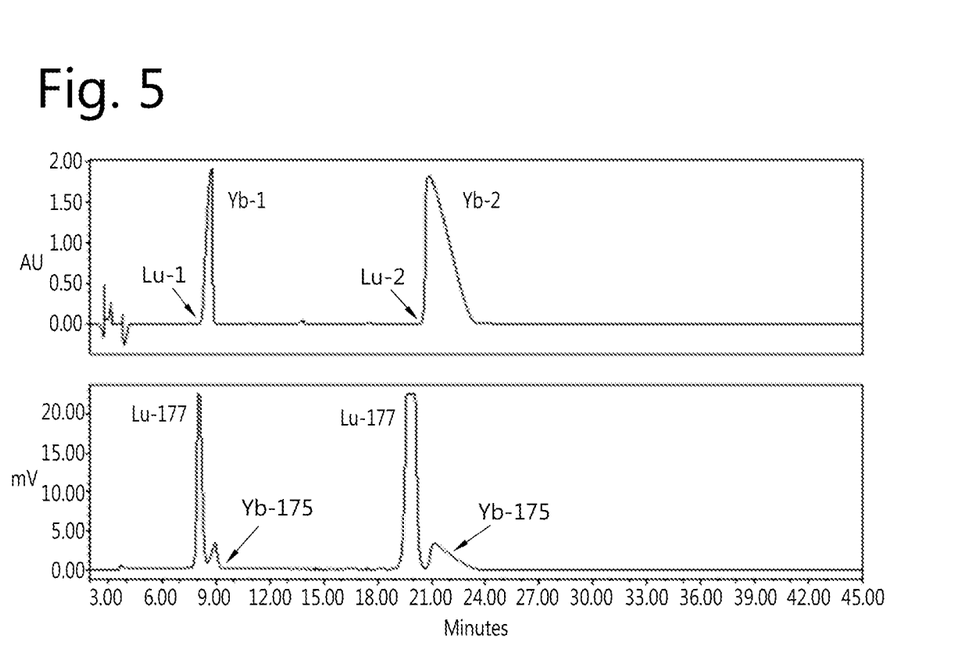
FIG. 5: Elution and separation of Lu and Yb using B501

Irradiated enriched Yb (enriched in Yb176, 99.3%) after irradiation Lu177 en Yb175 are formed. The mix of Lu and Yb is chelated with Oxo-chelator (B501). Both isotopes are visible at the same moment on the radiodetector (FIG. 5, bottom), Lu first, followed by Yb for both isomers. Due to the large excess of Yb, the UV detectors (FIG. 5 top) only shows the Yb-chelate (in the two isomers (1 and 2)). 1/100 part of the mixture was brought on the HPLC column. Top: UV detection (only bulk Yb visible); Bottom: Lu177 and Yb-175 visible. It is evident that Lu-177-oxo (B501) for both isomers elutes first followed by the corresponding Yb isomers. Radio detection and UV measurements are taking place at the same time, the two graphs hence represent the same separation.

Example 6

Irradiated enriched Yb (enriched in Yb176, 99.3%) after irradiation Lu177 en Yb175 are formed. The mix of Lu and Yb is chelated with PTCA-chelator (B401). Both isotopes are visible at the same moment on the radiodetector (FIG. 6, Top), Lu first, followed by Yb for both isomers. Due to the large excess of Yb, the UV detector only shows the Yb-chelate (in the two isomers (1 and 2)). ¹/₁₀₀₀ part of the mixture was brought on the HPLC column 4.6×250 mm column. Top: UV detection (only bulk Yb visible); Bottom: Lu177 and Yb175 visible. It is evident that Lu-177-PCTA (B401) for both isomers elutes first followed by the corresponding Yb-PCTA isomers. Radio detection and UV measurements are taking place at the same time, the two graphs hence represent the same separation.

Polasek demonstrates a separation of 0.158 mg Yb on a 10×250 mm column (example 93 of EP3492460 To come to a dose suitable for one patient, 20 mg Yb176 is necessary. A scale up is hence necessary (by a factor 100-1000) to come to a meaningful separation process. Loading higher amount of Yb on a column, by constant column volume, can lead to uncontrolled spread of the Yb chelate over the column, leading to massive peak fronting as well as tailing, whereby the Yb bulk can interfere and mix with Lu177. It is hence advantageous to load as much mass as possible on a column without affecting the effectiveness of the separation.

Example 7

Purification of 21 mg of irradiated Yb176 (enriched by 99.3% in Yb176) on a 50 mm column using PCTA chelator (B401). Irradiation results in 10.9 GBq Lu177 and 2.5 GBq Yb175. The ratio of Yb:Lu after irradiation is about 5000:1. The mixture is bound to PCTA derivative (B401) and loaded onto a 50×250 mm column.

Figure 6:
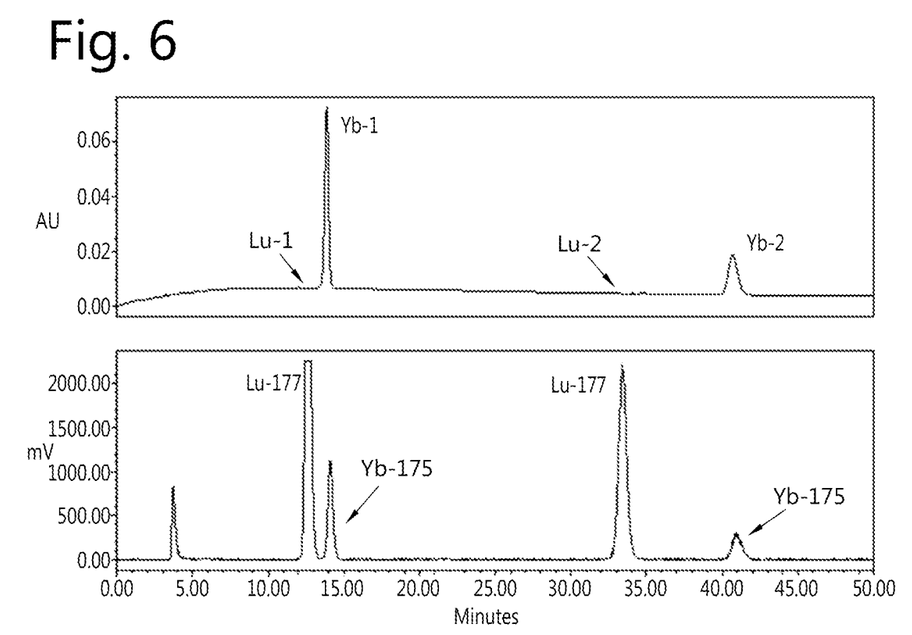
FIG. 6: Elution and separation of Lu and Yb using B401
Figure 7A:
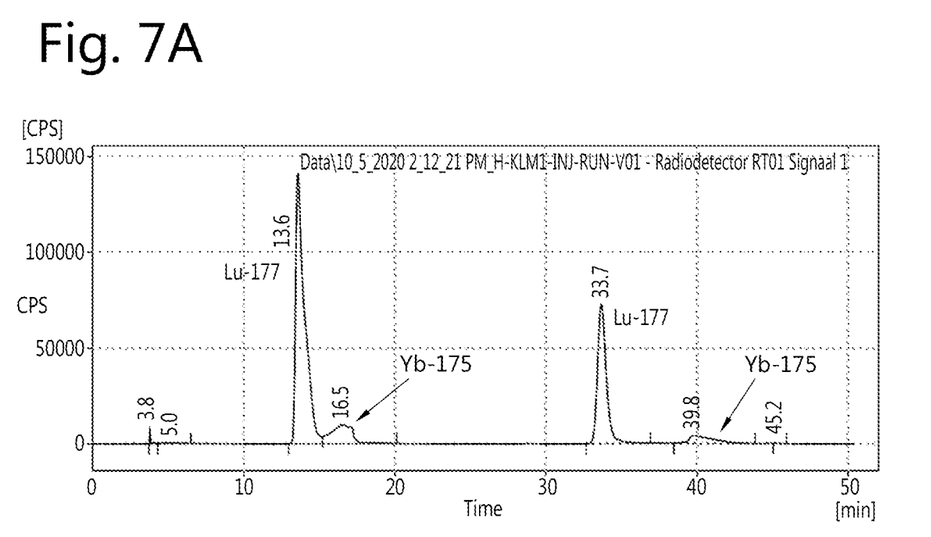
FIG. 7A: Separation of Lu-177 and Yb-175 in two isomers on patient dose basis using B401
Figure 7B:
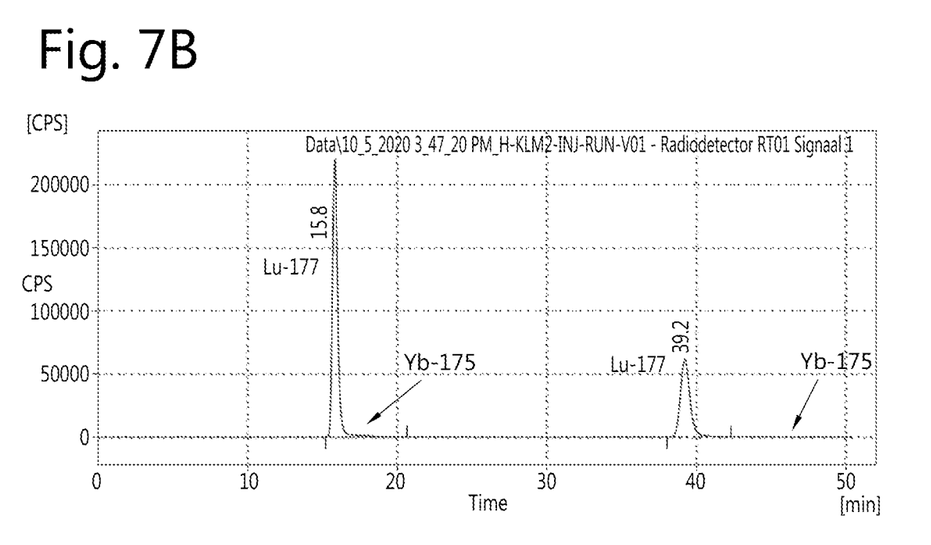
FIG. 7B: Separation of Lu-177 and Yb-175 after reinjection on patient dose basis

FIG. 7A. First column (radio detection). Lu177 fractions were collected for re-injection on a second column (FIG. 7B). After the second column, the overall recovery is 79% Lu177, with the Yb175 reduced to 0.007% after two columns (Yb removal factor 15,000). This demonstrates that the separation can be carried out on large scale. The chromatogram of example 7 is identical to the radiochromatogram in example 6. The process is stable and consistent at different scales Example 8

Figure 8A:
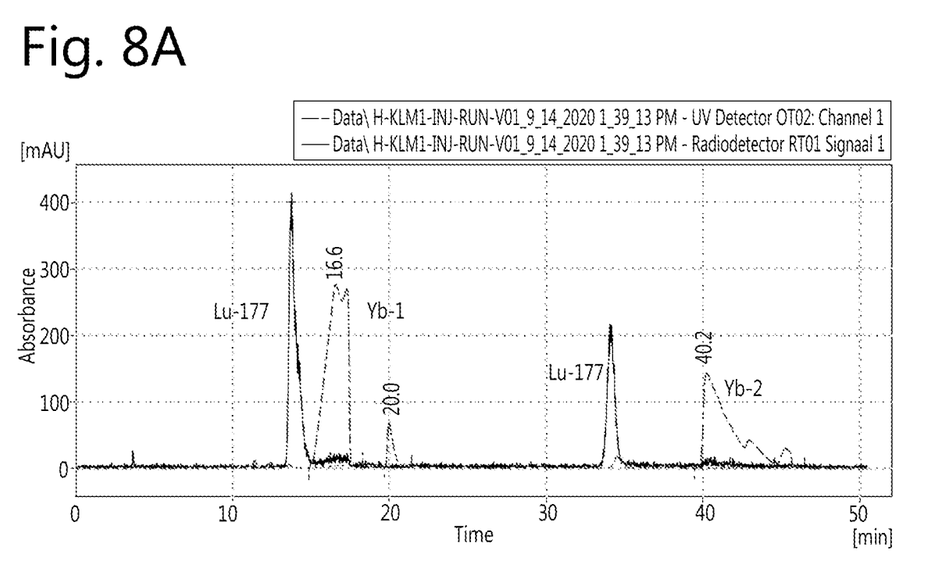
FIG. 8A: Scale up separation of Lu-177 and Yb-175 using B401 (with 20 mg of Yb)
Figure 8B:
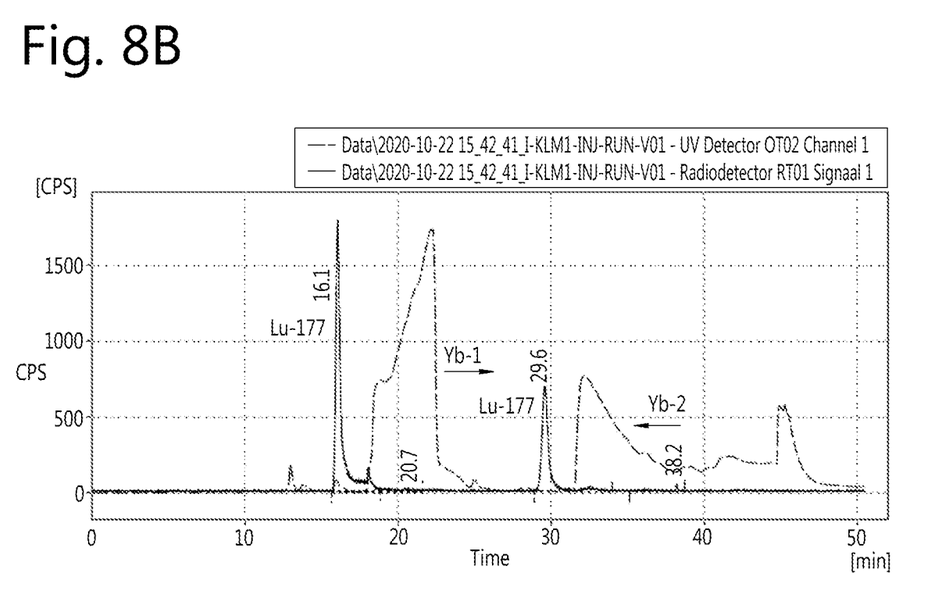
FIG. 8B: Scale up separation of Lu-177 and Yb-175 using B401 (with 200 mg of Yb)

To demonstrate the effect of a scale-up on the separation profile, a PCTA (B401)-chelate mixture of Yb and Lu177 in the ratio 5000:1 was made, with 20 mg of Yb (FIG. 8A) and 200 mg of Yb (FIG. 8B) loaded on a 50×250 mm column. FIG. 8B shows that the 1st Yb isomer moves away from the 1st Lu177 isomer during this 10× upscaling (to the right, slower elution), while the 2nd Yb isomer moves towards the 2nd Lu177 isomer (to the left, faster elution). This upscaling profile for PCTA (LC2; B401) and oxo (LC1; B501)) chelates is advantageous because the existing small baseline separation between the 1st isomers of Yb and Lu improves relatively on upscaling, while the smaller resolution between the 2nd isomers of Yb and Lu has no negative consequences because the resolution between the 2nd isomers of Yb and Lu is very high. By further adjusting the separation parameters, Yb masses>200 mg can be processed on a 50×250 mm column. The oxo (B501) chelators follow the same profile when scaled up.

This special property, in combination with the Lu—Yb elution sequence, indicates that PCTA (B401) and oxo (B501) chelators are very suitable for upscaling.

Example 9

Figure 9:
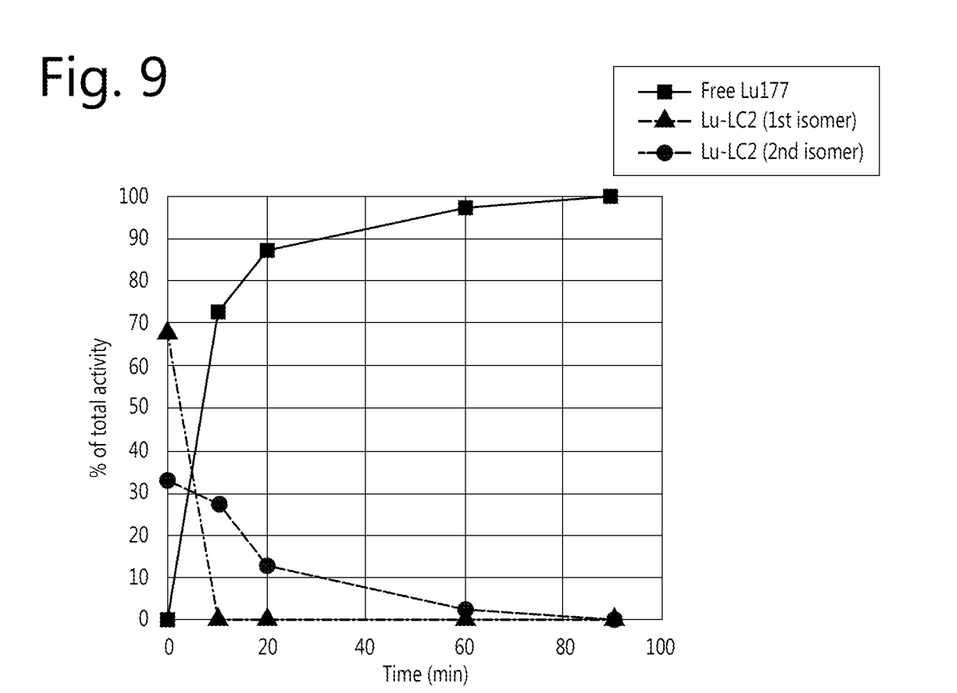
FIG. 9: Decomplexation profile

Decomplexation and Isomeric Ratio:
The mix of Lu-PCTA chelate of example 8 was incubated with 1 M HCl, at 70° C., to break the Lu177-chelate complex and produce free Lu177. FIG. 9 shows the amount of $1^{st}$ isomer (triangle), $2^{nd}$ isomer (circle) and free Lu177 overtime. In less than 10 minutes the $1^{st}$ isomer (triangle) is completely decomplexed. At the same time, the second, more stable, isomer remains still 85% intact. By increasing the pH to 8 at a desired time, the decomplexation will stop and the free Lu177 will complex again in the ratio 65% $1^{st}$ isomer and 35% $2^{nd}$ isomer. By repeating this process, the amount of the $2^{nd}$ isomer is increased and the $1^{st}$ isomer is decreased. This trans-chelation demonstrates that the isomer ratio can be influenced, for example to increase the most favorable isomer (depending on the resolution of the Lu/Yb chelates, the desired scale-up and the required separation process). The pattern for PCTA (B401) and Oxo (B501) is the same (2 isomers, elution order Lu—Yb and the shift on upscaling), but the isomer ratio and the resolution between the Lu and Yb isomers is different. The isomer ratio for oxo (B501) is 15% of the 1st isomer and 85% of the $2^{nd}$ isomer. The isomer ratio for PCTA (B401)-Lu/Yb chelates, is 65% of the 1st isomer and 35% of the $2^{nd}$ isomer. The ratio between $1^{st}$ and $2^{nd}$ isomer can be influenced because there is a difference between the stability of the $1^{st}$ and $2^{nd}$ isomers in an acidic environment.

The invention claimed is:
1. A compound of general formula (I):

wherein

A is N or C substituted with one of H, halogen (Cl, Br, F), SO$_3$H, C$_{1-4}$ alkyl, aryl, hetaryl, C—O—C$_{1-16}$ alkylamino,

Z and Z$^1$ independently are N or C substituted with one of H, halogen (Cl, Br, F), SO$_3$H, C$_{1-4}$ alkyl, aryl, hetaryl, C—O—C$_{1-16}$ alkylamino, E=O, S or P;

R$_1$ is independently substituted or unsubstituted C$_{4-15}$alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)(CH$_2$)0-3CH3, C$_{2-5}$carboxyl, —(CH$_2$)$_{1-3}$C(O)(CH$_2$)$_{0-3}$CH$_3$, nitro, amino, thiol, succinimide, maleimide, aminooxyl, acetylene, N$_3$, acetamino, azide, —C(O)O(CH$_2$)$_{1-3}$CH$_3$, —OC(O)(CH$_2$)$_{0-3}$CH$_3$, halogen, C$_{1-5}$alkynyl, and NCS;

and a=0-5.

2. The compound according to claim 1, wherein R₁ is wherein R₂ is independently H, —NCS, —OH, —NH₂, —C(O)NH₂, —NO₂, —(CH₂)₁₋₃O(CH₂)₁₋₃CH₃, —C(O)O(CH₂)₁₋₃CH₃, —OC(O)(CH₂)₀₋₃CH₃, halogen, —(CH₂)₁₋₃C(O)(CH₂)₀₋₃CH₃, cyano, C₂₋₅carboxyl, thiol, —C(O)(CH₂)₀₋₃CH₃, substituted or unsubstituted C₁₋₁₅alkyl, substituted or unsubstituted C₁₋₁₅alkenyl, substituted or unsubstituted C₁₋₁₅alkynyl, substituted or unsubstituted C₄₋₁₅alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)(CH₂)₀₋₃CH₃, C₂₋₅carboxyl, —(CH₂)₁₋₃C(O)(CH₂)₀₋₃CH₃, nitro, amino, thiol, succinimide, maleimide, aminooxyl, acetylene, N₃, acetamino, azide, —C(O)O(CH₂)₁₋₃CH₃, —OC(O)(CH₂)₀₋₃CH₃, halogen, C₁₋₅alkynyl, and NCS;

a=1-4,
and b=1-4.

3. Use according to claim 2, wherein R₂ is chosen from the group consisting of H, —NCS, —OH, —NH₂, —C(O)NH₂, —NO₂, —(CH₂)₁₋₃O(CH₂)₁₋₃CH₃, —C(O)O(CH₂)₁₋₃CH₃, —OC(O)(CH₂)₀₋₃CH₃, halogen, —(CH₂)₁₋₃C(O)(CH₂)₀₋₃CH₃, cyano, C₂₋₅carboxyl, thiol, and —C(O)(CH₂)₀₋₃CH₃.

4. The compound according to claim 3, wherein R₂ is —NH₂ or —NCS.

5. The compound according to claim 4, wherein the compound of general formula (I) is

6. The compound according to claim 5, wherein the compound of general formula (I) is -continued 7. A method of chromatographic separation of rare earth elements, actinides and/or s-, p- and d-block metals, from a mixture of at least two metal ions, the method comprising:
(a) providing a mixture of at least two different metal ions chosen from rare earth metal ions, actinide ions and/or s-, p- and d-block metal ions,
(b) forming chelates by contacting metal ions comprised in the mixture with at least one compound of general formula (I):

wherein

A is N or C substituted with one of H, halogen (Cl, Br, F), $SO_3H$, $C_{1-4}$ alkyl, aryl, hetaryl, C—O—$C_{1-16}$ alkylamino,
Z and $Z^1$ independently are N or C substituted with one of H, halogen (Cl, Br, F), $SO_3H$, $C_{1-4}$ alkyl, aryl, hetaryl, C—O—$C_{1-16}$ alkylamino,
E=O, S or P;
$R_1$ is independently substituted or unsubstituted $C_{4-15}$alkylaryl, substituted or unsubstituted aryl, substituted or unsubstituted heterocycle, or substituted or unsubstituted heteroaryl, wherein the substitution is by one or more moiety(ies) selected from a group consisting of imide, —C(O)(CH$_2$)0-3CH3, $C_{2-5}$carboxyl, —(CH$_2$)$_{1-3}$C(O)(CH$_2$)$_{0-3}$CH$_3$, nitro, amino, thiol, succinimide, maleimide, aminooxyl, acetylene, $N_3$, acetamino, azide, —C(O)O(CH$_2$)$_{1-3}$CH$_3$, —OC(O)(CH$_2$)$_{0-3}$CH$_3$, halogen, $C_{1-5}$alkynyl, and NCS; and a=0-5;
(c) subjecting the chelates to chromatographic separation, wherein optionally at least one separated metal chelate can be subjected to at least one further chromatographic separation in order to increase the purity of the at least one separated metal chelate;
and, optionally,
(d) obtaining the metal from the at least one separated metal chelate.

8. The method of chromatographic separation according to claim 7, wherein the mixture of at least two different metal ions to be separated comprises at least one rare earth element.

9. The method of chromatographic separation according to claim 7, wherein the mixture of at least two different metal ions to be separated comprises two neighbouring lanthanides.

10. The method of chromatographic separation according to claim 7, wherein the mixture of at least two different metal ions to be separated comprises Lu and Yb, or Tb and Gd.

11. The method of chromatographic separation according to claim 10, wherein the mixture of at least two different metal ions to be separated comprises 177Lu and 176Yb, or 161Tb and 160Gd.

12. The method of chromatographic separation according to claim 7, wherein the chromatographic separation is with column chromatography, thin layer chromatography and/or high-performance liquid chromatography.

13. The method of chromatographic separation according to claim 7, wherein metal ions are in a form of salts of organic or inorganic acids, oxides, hydroxides and/or carbonates.

14. The method chromatographic separation according to claim 7, wherein metal ions are in a form of salts selected from the group consisting of chloride, bromide, sulfate, nitrate, methanesulfonate, trifluoromethanesulfonate, formate, acetate, lactate, malate, citrate, 2-hydroxyisobutyrate, mandelate, diglycolate, tartarate, oxide, hydroxide and carbonate.

15. The method of chromatographic separation according to claim 7, wherein a solution containing the mixture in the form of metal salts, or a solid phase containing the mixture in the form of metal oxide, hydroxide and/or carbonate, is mixed with a solution of the compound of general formula (I) in molar ratio of metal ions to compound of general formula (I) from 1:0.5 to 1:100.

16. The method of chromatographic separation according to claim 15, further comprising adding organic or inorganic base to the reaction mixture, allowing complexation to occur in the solution.

* * * * *